United States Patent [19]

Nohr et al.

[11] Patent Number: 5,382,703
[45] Date of Patent: Jan. 17, 1995

[54] ELECTRON BEAM-GRAFTABLE COMPOUND AND PRODUCT FROM ITS USE

[75] Inventors: Ronald S. Nohr, Roswell; John G. MacDonald; Laura E. Herring, both of Decatur, all of Ga.

[73] Assignee: Kimberly-Clark Corporation, Neenah, Wis.

[21] Appl. No.: 972,656

[22] Filed: Nov. 6, 1992

[51] Int. Cl.⁶ ............................................. C07C 43/11
[52] U.S. Cl. ..................................... 568/609; 568/611
[58] Field of Search ............................... 568/609, 611

[56] References Cited

U.S. PATENT DOCUMENTS

| | | | |
|---|---|---|---|
| 2,999,056 | 9/1961 | Tanner | 204/154 |
| 3,016,599 | 1/1962 | Perry, Jr. | 28/78 |
| 3,341,394 | 9/1967 | Kinney | 161/72 |
| 3,655,862 | 4/1972 | Dorschner et al. | 264/290 |
| 3,692,618 | 9/1972 | Dorschner et al. | 161/72 |
| 3,704,198 | 11/1972 | Prentice | 161/148 |
| 3,705,068 | 12/1972 | Dobo et al. | 156/441 |
| 3,755,527 | 8/1973 | Keller et al. | 264/210 |
| 3,802,817 | 4/1974 | Matsuki et al. | 425/66 |
| 3,849,241 | 11/1974 | Butin et al. | 161/169 |
| 3,853,651 | 12/1974 | Porte | 156/73.6 |
| 3,973,068 | 8/1976 | Weber | 428/198 |
| 3,978,185 | 8/1976 | Buntin et al. | 264/93 |
| 4,064,605 | 12/1977 | Akiyama et al. | 28/103 |
| 4,070,218 | 1/1978 | Weber | 156/167 |
| 4,091,140 | 5/1978 | Harmon | 428/288 |
| 4,100,309 | 7/1978 | Micklus et al. | 427/2 |
| 4,100,319 | 7/1978 | Schwartz | 428/171 |
| 4,100,324 | 7/1978 | Anderson et al. | 428/288 |
| 4,118,531 | 10/1978 | Hauser | 428/224 |
| 4,340,563 | 7/1982 | Appel et al. | 264/518 |
| 4,405,297 | 9/1983 | Appel et al. | 425/72 |
| 4,434,204 | 2/1984 | Hartman et al. | 428/198 |
| 4,627,811 | 12/1986 | Greiser et al. | 425/72 |
| 4,644,045 | 2/1987 | Fowells | 526/348 |
| 4,663,220 | 5/1987 | Wisneski et al. | 428/221 |

FOREIGN PATENT DOCUMENTS

23810 12/1961 Japan .
839483 6/1960 United Kingdom .

OTHER PUBLICATIONS

CA 107(21):197701n, "Cetyltrimethyl Ammonium Permanganate; a Useful Reagent . . . ", Rathore, et al., J. Chem. Res., 458–9, 1986.

R. Rathore et al., *J. Chem. Research (S)*, 1986, 458–459.
V. A. Wente et al, "Manufacture of Superfine Organic Fibers", Navy Research Laboratory, Washington, D.C., NRL Rpt. 4364, (111437), dtd May 25, 1954, U.S. Dept. of Comm., Office of Tech. Svcs.
Robert R. Butin and Dwight T. Lohkamp, "Melt Blowing-A One-Step Web Process for New Nonwoven Products", Journal of the Technical Assoc. of the Pulp and Paper Ind., vo. 56, No. 4, pp. 74–77, 1973.
P. Alexander et al., Proc. Royal Soc. London, 1954, A223, 892.
F. A. Bovey, "The Effects of Ionizing Radiation on Natural and Synthetic High Polymers Review Series," 1958, 1, Interscience, N.Y.
S. G. Hall et al, Textile Chemist and Colorist, 1977, vol. 9, 1977.
Z. Foltynoxicz, et al, Macromolecules, 1985, 18 1394.
A. Baszkin, et al., J. Colloid Interface Science, 1973, 43, 190.
V. A. Wente, "Superfine Thermoplastic Fibers", *Industrial and Engineering Chemistry*, vol. 48, No. 8, pp. 1342–1346 (1956).

*Primary Examiner*—Bernard Lipman
*Attorney, Agent, or Firm*—William E. Maycock

[57] ABSTRACT

A compound of the formula:

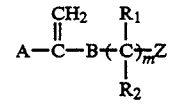

in which:
 (a) each of A and B independently is phenyl which may be unsubstituted or substituted;
 (b) each of $R_1$ and $R_2$ independently is hydrogen or $C_1-C_6$ alkyl;
 (c) m represents an integer of from 0 to about 18; and
 (d) Z is poly(alkyleneoxy) which may be uncapped or capped with a $C_1-C_6$ alkyl group.

The compound can be grafted to polyolefin nonwoven webs by electron beam radiation without significant homopolymerization. The grafted webs are wettable (hydrophilic) and capable of withstanding multiple rewets without substantial removal of grafted compound. The grafted webs are especially well-suited for use in disposable absorbent products.

4 Claims, 5 Drawing Sheets

ELECTRON BEAM-GRAFTABLE COMPOUND AND PRODUCT FROM ITS USE

BACKGROUND OF THE INVENTION

The present invention relates to an electron beam-graftable compound. More particularly, the present invention relates to a compound which can be grafted to a hydrophobic surface under electron beam radiation without homopolymerizing, thereby altering the surface characteristics of the hydrophobic surface.

Polymers are used widely throughout the world to make a variety of products which include blown and cast films, extruded sheets, injection molded articles, foams, blow molded articles, extruded pipe, monofilaments, and nonwoven webs. Some of such polymers, such as polyolefins, are naturally hydrophobic, and for many uses this property is either a positive attribute or at least not a disadvantage.

There are a number of uses for polyolefins, however, where their hydrophobic nature either limits their usefulness or requires some effort to modify the surface characteristics of the shaped articles made therefrom. By way of example, polyolefins are used to manufacture nonwoven webs which are employed in the construction of such disposable absorbent articles as diapers, feminine care products, incontinence products, wipes, and the like. Frequently, such nonwoven webs need to be wettable, especially when the webs are to be used as, by way of example only, diaper liners, feminine pad transfer layers, tampon covers, and industrial wipes.

The wettability of normally hydrophobic nonwoven webs can be obtained by spraying or coating the web with a surfactant solution during or after its formation. The web then must be dried, and the surfactant which remains on the web is removed upon exposure of the web to aqueous media; thus, the imparted hydrophilicity is transient and cannot withstand multiple wettings.

Alternatively, a surfactant can be included in the polymer which is to be melt-processed, as disclosed in U.S. Pat. Nos. 3,973,068 and 4,070,218 to Weber. In that case, however, the surfactant must be forced to the surface of the fibers from which the web is formed. This typically is done by heating the web on a series of steam-heated rolls or "hot cans". This process, called "blooming", is expensive and still has the disadvantage of ready removal of the surfactant by aqueous media. Moreover, the surfactant has a tendency to migrate back into the fiber which adversely affects shelf life, particularly at high storage temperatures. In addition, it is not possible to incorporate in the polymer levels of surfactant much above 1 percent by weight because of severe processability problems; surfactant levels at the surface appear to be limited to a maximum of about 0.33 percent by weight. Most importantly, the blooming process results in web shrinkage in the cross-machine direction and a significant loss in web tensile strength.

Chemically modifying the surfaces of fibers and nonwoven webs has been achieved by radiation-induced polymerization and also by chemical reactions at the fiber surfaces. For example, the irradiation of polymerizable materials can result in the formation of block or graft interpolymers due to cross-linking (abstraction of $\alpha$-methylenic hydrogen atoms) or chain scission between carbon-carbon bonds; see, e.g., P. Alexander et al., *Proc. Royal Soc. (London)*, 1954, A223, 892.

The efficiency of actual grafting, however, depends on the relative susceptibilities of the monomer and polymer to the ionizing energy. For example, if the number of radicals per 100 electron volts (eV) of absorbed ionizing energy for the monomer is much greater than that of the polymer, homopolymerization will predominate with little or no grafting. See F. A. Bovey, "The Effects of Ionizing Radiation on Natural and Synthetic High Polymers Review Series," 1958, 1, Interscience, N.Y.

Typical methods of irradiation-induced grafting employed in the surface modification of polymers are as follows:

(a) the simultaneous irradiation of polymer in the presence of excess monomer;

(b) the irradiation of polymer prodipped in monomer;

(c) the pre-irradiation of polymer (in the absence of oxygen), followed by exposure to monomer; and (d) the pre-irradiation of the polymer in air to form peroxides which subsequently decompose in the presence of monomer.

A number of vinylic monomers have been grafted onto polypropylene fibers. See, by way of illustration, Japanese Patent No. 23810, 1961; U.S. Pat. No. 2,999,056 to Tanner; and British Patent No. 839,483. For example, glycidyl methacrylate or acrylate was grafted by irradiation onto polypropylene fibers containing benzophenone. Polyethylene film has been grafted with acrylic acid by both simultaneous irradiation and pre-irradiation techniques.

The use of synthetic fibers in apparel fabrics has led to heightened interest in the aspects of hydrophilic surfaces that relate to comfort, such as softness, wicking, absorption of water, and transport of moisture through and from the body. Much work, for example, has been reported on making polyester fabrics (woven or non-woven) as comfortable as cotton (S. G. Hall et at., *Textile Chemist and Colorist*, 1977, 9, 20). To achieve this objective, methods were developed to chemically polymerize several hydrophilic monomers on polyester fabrics to give cross-linked finishes having various ionic and nonionic groups. The finishes are swellable and give fabrics the ability to hold large amounts of water without a significant restriction on wicking. Nylon fabrics also can be made hydrophilic by means of the same procedure.

In addition, numerous papers have been published on how to make polyolefins (such as polyethylene and polypropylene) hydrophilic using irradiation procedures. See, for example, Z. Foltynoxicz et al., *Macromolecules*, 1985, 18, 1394; U.S. Pat. No. 4,100,309 to Micklus et al.; and A. Baszkin et al., *J. Colloid Interfce Science*, 1973, 43, 190. As of now, most of the developments have centered on coating or impregnating the hydrophilic species onto the substrates. These coated or impregnated surfaces, however, typically are not permanent and often are removed if organic or aqueous solvents come in contact with the treated substrates.

In summary, most coatings for electron beam work involve simple vinyl-or acrylate-based chemistry. On exposure to electron beam radiation (or other radical-generating source), the primary reaction is one of homopolymerization. The resulting homopolymer is simply trapped in the void spaces of the nonwoven web. This is deleterious for the following reasons:

(a) there is a stiffening of the fabric, or loss of drape;

(b) There is little or no modification of the fiber surfaces;

(c) The fabric has the surface properties of both the homopolymer and the original, typically hydrophobic fabric; and (d) there typically is a loss of or reduction in fabric porosity.

Several radiation technologies other than electron beams have been used to chemically modify the surfaces of polymeric materials to achieve such hydrophilicity, but with varying disadvantages. Ultraviolet and cobalt-60 gamma radiation are mainly applied to substrates immersed in aqueous solutions or other solvent systems. Radio-frequency plasma radiation treatments may be carried out with gaseous materials, but at low pressures.

Electron beam radiation, however, is the radiation treatment of choice. Electron beam radiation can be applied as part of a semi-dry process without solvents, and its fast reaction time ($10^{-2}$ sec) makes it suitable for an on-line continuous process. Interaction of electron-beam radiation with a polymeric material generates free radicals on the polymer surface. These free radicals will attack vinylic species present on the surface, making possible the attachment of surface-modifying moieties to a polymeric substrate. However, the efficiency of this grafting reaction is dependent upon the tendency of the monomer to homopolymerize, or react with itself instead of the substrate.

A new class of compounds has been discovered for use with an electron beam process which cannot significantly homopolymerize because of the steric hindrance designed into the molecular structure. However, the compounds still undergo rapid radical formation with the concomitant grafting of the compounds onto the surfaces of fibers and nonwoven webs. Thus, significant and permanent changes in the surface characteristics of the fibers and nonwoven webs are possible without the foregoing disadvantages typically associated with radiation-induced surface modification techniques.

SUMMARY OF THE INVENTION

It therefore is an object of the present invention to provide a new class of compounds which cannot significantly homopolymerize under the influence of electron beam radiation.

It is another object of the present invention to provide a method of modifying the surfaces of fibers and nonwoven webs by means of electron beam radiation.

It is a further object of the present invention to provide fibers and nonwoven webs to which a novel compound has been grafted in order to render the webs hydrophilic.

These and other objects will be apparent to one having ordinary skill in the art from a consideration of the specification and claims which follow.

Accordingly, the present invention provides a compound of the formula:

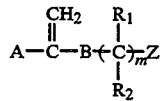

in which:
(a) each of A and B independently is phenyl which may be unsubstituted or substituted;
(b) each of $R_1$ and $R_2$ independently is hydrogen or $C_1$–$C_6$ alkyl;
(c) m represents an integer of from 0 to about 18; and
(d) Z is poly(alkyleneoxy) which may be uncapped or capped with a $C_1$–$C_6$ alkyl group.

In certain desired embodiments, each of A and B is an unsubstituted phenyl group. In still other desired embodiments, m represents an integer of from 0 to about 5.

DETAILED DESCRIPTION OF THE INVENTION

Figure 1:
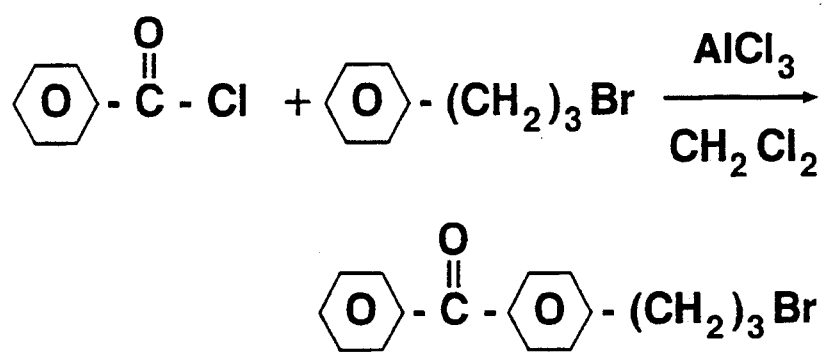
FIGS. 1–10 illustrate the various chemical reactions involved in preparing the compounds of the examples.

The compound provided by the present invention can be represented by the following general formula:

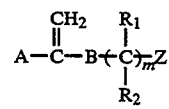

Each of A and B independently is phenyl which may be unsubstituted or substituted. If desired, either or both of A and B can be substituted with one or more monovalent groups which do not adversely affect the grafting reaction (i.e., free radical formation), web characteristics, and the like. Desirably, such monovalent groups independently are selected from the group consisting of $C_1$–$C_6$ alkyl, $C_4$–$C_7$ cycloalkyl, halo, alkoxy, and phenoxy groups. Both A and B more desirably are unsubstituted.

Each of $R_1$ and $R_2$ independently is hydrogen or $C_1$–$C_6$ alkyl. Desirably, each of $R_1$ and $R_2$ independently is hydrogen or $C_1$–$C_3$ alkyl, of which hydrogen is more desired.

In general, m represents an integer of from 0 to about 18. Desirably, m represents an integer of from 0 to about 5.

Z is poly(alkyleneoxy) which may be uncapped or capped with a $C_1$–$C_6$ alkyl group. In certain desired embodiments, Z can be represented by the general formula,

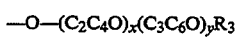

in which x represents an integer of from about 3 to about 18, y represents an integer of from 0 to about 9, the ratio of x to y is equal to or greater than 2; the sum of x and y is equal to or less than about 18; and $R_3$ is hydrogen or $C_1$–$C_6$ alkyl. In particularly desired embodiments, $R_3$ is methyl, y is zero, and x represents an integer in the range of from about 7 to about 14.

To graft a compound of the present invention to a nonwoven web by means of electron beam radiation, the compound is dissolved in a suitable solvent or solvent mixture, the nonwoven web is treated with the resulting solution, the solvent optionally is removed from the web, and the treated web is exposed on either or both sides to an amount of electron beam radiation sufficient to graft the compound to the surfaces of the fibers.

As used herein, the term "nonwoven web" means a web prepared by a traditional melt-extrusion process from a thermoplastic polymer, which process typically involves melting the thermoplastic polymer, extruding the molten polymer through a plurality of orifices to form a plurality of threadlines or filaments, attenuating the filaments by entrainment in a rapidly moving first stream of gas, cooling the filaments with a second stream of gas, and randomly depositing the attenuated filaments, or fibers, on a moving foraminous surface. The most common and well known of these processes are meltblowing, colorming, and spunbonding. The term also includes bonded, carded webs.

Meltblowing references include, by way of example, U.S. Pat. No. 3,016,599 to Perry, Jr., U.S. Pat. No. 3,704,198 to Prentice, U.S. Pat. No. 3,755,527 to Keller et al., U.S. Pat. No. 3,849,241 to Butin et at., U.S. Pat. No. 3,978,185 to Butin et al., and U.S. Pat. No. 4,663,220 to Wisneski et al. See, also, V. A. Wente, "Superfine Thermoplastic Fibers", *Industrial and Engineering Chemistry*, Vol. 48, No. 8, pp. 1342–1346 (1956); V. A. Wente et al., "Manufacture of Superfine Organic Fibers", Navy Research Laboratory, Washington, D.C., NRL Report 4364 (111437), dated May 25, 1954, United States Department of Commerce, Office of Technical Services; and Robert R. Butin and Dwight T. Lohkamp, "Melt Blowing—A One-Step Web Process for New Nonwoven Products", *Journal of the Technical Association of the Pulp and Paper Industry*, Vol. 56, No.4, pp. 74–77 (1973).

Coforming references (i.e., references disclosing a meltblowing process in which fibers or particles are comingled with the meltblown fibers as they are formed) include U.S. Pat. No. 4,100,324 to Anderson et al. and U.S. Pat. No. 4,118,531 to Hauser.

Finally, spunbonding references include, among others, U.S. Pat. No. 3,341,394 to Kinney, U.S. Pat. No. 3,655,862 to Dorschner et al., U.S. Pat. No. 3,692,618 to Dorschner et al., U.S. Pat. No. 3,705,068 to Dobo et al., U.S. Pat. No. 3,802,817 to Matsuki et al., U.S. Pat. No. 3,853,651 to Porte, U.S. Pat. No. 4,064,605 to Akiyama et al., U.S. Pat. No. 4,091,140 to Harmon, U.S. Pat. No. 4,100,319 to Schwartz, U.S. Pat. No. 4,340,563 to Appel and Morman, U.S. Pat. No. 4,405,297 to Appel and Morman, U.S. Pat. No. 4,434,204 to Hartman et al., U.S. Pat. No. 4,627,811 to Greiser and Wagner, and U.S. Pat. No. 4,644,045 to Fowels.

The polymers most often used in the foregoing processes, particularly for the types of products mentioned, are polyolefins. These polymers are naturally hydrophobic, which often is an undesirable characteristic.

In general, the term "thermoplastic polyolefin" is used herein to mean any thermoplastic polyolefin which can be used for the preparation of nonwoven webs. Examples of thermoplastic polyolefins include polyethylene, polypropylene, poly(1-butene), poly(2-butene), poly(1-pentene), poly(2-pentene), poly(3- methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, and the like.

The more desired polyolefins are those which contain only hydrogen and carbon atoms and which are prepared by the addition polymerization of one or more unsaturated monomers. Examples of such polyolefins include, among others, polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polystyrene, and the like. In addition, such term is meant to include blends of two or more polyolefins and random and block copolymers prepared from two or more different unsaturated monomers. Because of their commercial importance, the most desired polyolefins are polyethylene and polypropylene.

The solvent is not known to be critical, provided it does not react with the either the compound or the fibers of the web. The more desired solvents are the lower alcohols, such as methanol, ethanol, propanol, isopropanol, and the like. However, other polar solvents, such as tetrahydrofuran; N,N-dimethylformamide; 1,4-dioxane; 1-methyl-2-pyrrolidinone; the lower aliphatic ethers, such as ethyl ether, methyl ether, methyl ethyl ether, isopropyl ether, methyl propyl ether, and the like; halogenated hydrocarbons, such as chloroform, the Freon ® solvents, and the like; and the lower alkyl ketones, such as acetone, diethyl ketone, methyl ethyl ketone, dibutyl ketone, and the like can be utilized, if desired. The solids content of the solution also is not known to be critical, but typically will be limited by the solubility of the compound in the solvent and the method of application of the solution to the web. As a practical matter, the solids content of the solution will be in the range of from about 1 to about 5 percent by weight, although lower or higher concentrations can be employed.

The solution of the compound can be applied to the nonwoven web by any known means, such as spraying, printing, brushing, rolling, dipping, and the like. When it is desired to coat all of the fibers of the web, dipping or bathing the web in the solution, followed by running the web through a nip roll to remove excess solution, is especially appropriate.

The treated web can be subjected to electron beam radiation with or without retained solvent. A solvent removal step may be desired in order to permit the recovery and reuse of solvent and to help minimize loss of solvent into the atmosphere. In general, retained solvent can be removed by any means known to those having ordinary skill in the art. Such means include, by way of example, simple evaporation at atmospheric pressure, desirably under a fume hood; evaporation under reduced pressure; heating by infrared radiation, convection oven, forced air oven, or a microwave oven; and the like.

Finally, the treated web is exposed on either or both sides to an amount of electron beam radiation sufficient to graft the compound to the surfaces of the fibers. In general, the amount of radiation received by the web is a function of both the time of exposure and the intensity or energy of the radiation. Thus, the amount of radiation may be increased by increasing the time of exposure, the energy of the electrons, or both. Alternatively, multiple exposures to the same electron beam or the use of more than one electron beam source can be employed. Optimum conditions for any given compound can be determined readily by those having ordinary skill in the art without undue experimentation.

The present invention is further described by the examples which follow. Such examples, however, are not to be construed as limiting in any way either the spirit or scope of the present invention. In the examples, all temperatures are in degrees Celsius and all parts are by weight unless specified otherwise.

Examples 1 and 2 describe the preparation of two compounds coming within the scope of the present invention. The reaction scheme for each reaction or step is illustrated in a figure which is identified in the heading for that step. However, such figure is not discussed separately since it serves only to illustrate the reaction. Example 3 then describes the grafting of the two compounds on polypropylene nonwoven webs. All elemental analyses reported in the examples were car-

EXAMPLE 1

Synthesis of 14-[p-(1-Phenylvinyl)phenyl]-2,5,8,11-Tetraoxatetradecane

A. Synthesis of 4-(3-Bromopropyl)benzophenone (FIG. 1)

A three-necked, 1000-ml, round-bottomed flask was equipped with a 500-ml pressure-equalizing addition funnel, a Liebig condenser, and a gas inlet valve. A football-type, teflon-covered magnetic stirring bar was placed in the flask. The addition funnel was capped with a rubber septum. A calcium sutfate (8 Mesh Drierite®, Fisher Scientific Corp., Pittsburgh, Pa.) drying tube was fixed to the top of the condenser, and Tygon® tubing was used to connect the drying tube to a paraffin oil bubbler which in turn was connected to a nitrogen cylinder. A cork ring was placed between the round-bottomed flask and a magnetic stirring plate. Dry nitrogen was introduced to the system and allowed to flow through it while the glassware was dried with a heat gun for 30 minutes.

Approximately 300 ml of anhydrous dichloromethane was introduced to the addition funnel. using a cannula transfer from an Aldrich® Sure/Seal TM bottle (Aldrich Chemical Company, Milwaukee, Wisc.). The dichloromethane was allowed to flow into the round-bottomed flask below.

The nitrogen flow was increased and the condenser removed to allow the addition to the flask of 135 g (0.68 mole) of 1-bromo-3-phenylpropane (Fluka Chemical Corporation, Ronkonkoma, N.Y.). The condenser was quickly reattached and the nitrogen flow reduced.

Approximately 300 ml of dichloromethane was transferred to the addition funnel by cannula, followed by the addition of 100 g (0.71 mole) of benzoyl chloride (Aldrich) through a cone funnel to the addition funnel. The liquids were allowed to mix before the septum was again removed and 95 g (0.71 mole) of anhydrous aluminum Chloride (Aldrich) was added through a cone funnel. The mixture in the addition funnel turned brown as the Friedel-Crafts complex formed. The cannula was hooked up to the nitrogen flow and inserted through the septum into the aluminum chloride sediment at the bottom of the addition funnel to facilitate mixing.

After all of the aluminum chloride dissolved, the complex was added dropwise to the round-bottomed flask, with stirring, over a period of 2-3 hours. No detectable heat evolved, but moist litmus indicated acid release through the nitrogen outlet. The reaction mixture was allowed to stir at ambient temperature overnight.

The dark brown reaction mixture then was poured with stirring into two 1-liter portions of 10% by volume aqueous hydrochloric acid. In each case, the resulting mixture separated into two layers. The bottom (yellow) layers were isolated with the aid of a separatory funnel, and stirred for one hour with 10% by weight aqueous sodium bicarbonate. A 1000-ml separatory funnel again was used to isolate the organic phases, which were combined and then dried over anhydrous magnesium sulfate. The solvent was removed under reduced pressure; the yield of dark brown, viscous material was 190 g (93% ).

The crude product thus obtained was vacuum distilled over high temperature silicone oil (Aldrich) to give 4-(3-bromopropyl)benzophenone. The first and only fraction collected was a yellow oil that distilled at 167° (0.05 mm Hg). The yield was 61%. The analytical data, given below, were consistent with the assigned structure.

Infrared maxima of neat material: 3066, 3040, 2954, 1660, 1606, 1440, 1395, 1300, 1275, 1170, 933,917, and 699 cm$^{-1}$.

NMR (CDCl$_3$, 250 MHz): 2.17 ppm (q, 2H, J=6.75 Hz), 2.86 (t, 2H, J=7.4 Hz), 3.40 (t, 2H, J=6.5 Hz), and 7.3-7.8 (m, 9H).

Elemental Analysis: Calculated for C$_{16}$H$_{15}$OBr - C, 63.37; H, 4.95; Br, 26.40. Found - C, 66.26 and 65.93; H, 5.08 and 5.29; Br, 22.24 and 22.11.

Figure 2:
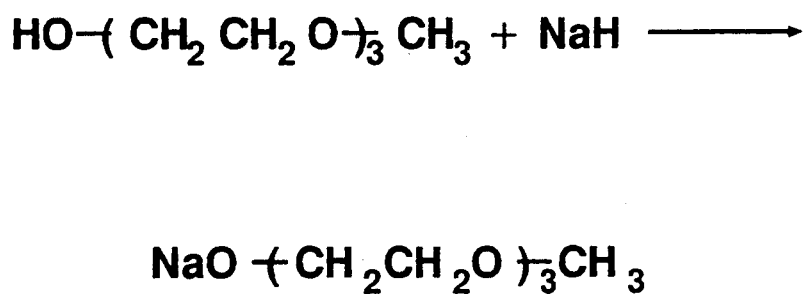

B. Alkoxylation of Triethylene Glycol Monomethyl Ether (FIG. 2)

A three-necked. 500-ml, round-bottomed flask was equipped with a nitrogen inlet, Liebig condenser, and a 125-ml pressure-equalizing addition funnel. A football-shaped magnetic stirring bar was placed in the flask. Tetrahydrofuran (THF, Aldrich) was collected after drying in a sodium benzophenone still, 150 ml of which were added to the flask. Sodium hydride (Aldrich), 2.4 g (0.10 mole), was added to the flask in one portion. Then 16.1 g (0.10 mole) of triethylene glycol monomethyl ether (Fluka) was placed in the addition funnel and added drop-wise to the flask over a 15-minute period. Heat and hydrogen evolved, and the solution turned from grey to beige, then dark brown. The reaction mixture was allowed to stir gently for two hours at ambient temperature, and then was used directly in the next step.

Figure 3:
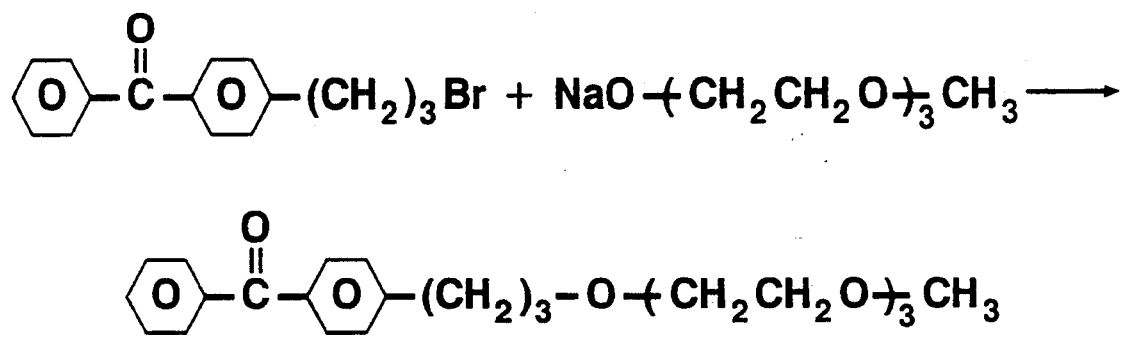

C. Williamson Ether Synthesis (FIG. 3)

Two hours after completion of the triethylene glycol addition, the empty addition funnel was replaced with one containing 27.0 g (0.09 mole) of 4-(3bromopropyl)-benzophenone from Step A. Heat was evolved, and the mixture turned black as the bromide was added dropwise to the reaction mixture from Step B containing the alkoxide, sodium 2-[2-(2-methoxyethoxy)ethoxy]ethoxde. The ensuing reaction was exothermic and the mixture began to reflux; it changed to a lighter, creamier brown color as sodium bromide formed. The reaction mixture was allowed to stir for 14 hours at ambient temperature.

The reaction mixture was filtered to remove the sodium bromide which was washed with THF; the THF washing was added to the reaction mixture filtrate and then the THF was removed in a rotary evaporator. The dark red liquid residue was shaken with a mixture of water and ethyl ether in a separatory funnel, and the resulting emulsion was broken with calcium chloride. The light orange ether layer was separated from the aqueous layer, dried over anhydrous magnesium sulfate, and filtered. The solvent was removed in a rotary evaporator, yielding 38.1 g of a dark orange liquid.

A column separation was performed, using 100-200 mesh silica gel (Fisher) and a 90% hexane/10% ethyl acetate mixture by volume as eluant. This elution removed unreacted 4-(3-bromopropyl)benzophenone. Material remaining on the column was eluted with ethyl acetate. The yield of benzophenone ether, 4-[3-[2-[2-(2-methoxyethoxy)ethoxy]ethoxy]propyl]benzophenone, was 50%. The analytical data, given below, were consistent with the assigned structure.

Infrared maxima of neat material: 3517, 3048, 2863, 1700, 1660, 1606, 1429, 1404, 1333, 1310, 1269, 1112, 943, 921,857, 750, and 703 cm$^{-1}$.

NMR (CDCl$_3$, 250MHz): 1.95 ppm (m, 2H), 2.78 (t, 2H, J=7.4), 3.37 (s, 3H), 3.41–3.66 (m, 13H), and 7.3–7.8 (m, 9H).

Figure 4:
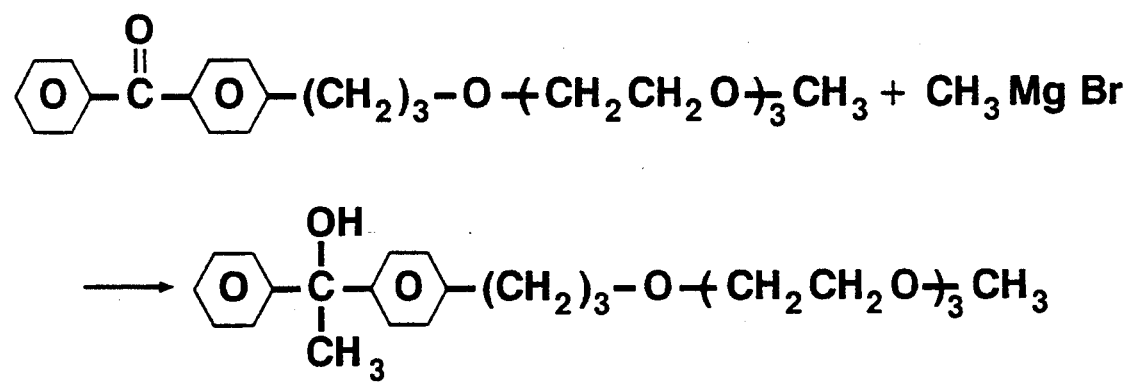

D. Synthesis of Tertiary Alcohol by Grignard Reaction (FIG. 4)

A 250-ml, three-necked, round-bottomed flask was equipped with a Liebig condenser, nitrogen inlet, and 125-ml, pressure-equalizing addition funnel. A football-shaped magnetic stirring bar was placed in the flask. A drying tube was filled with anhydrous calcium sulfate (Drierite) and attached to the top of the condenser, with an outlet tube for nitrogen flow. A cork ring was placed between the round-bottomed flask and a magnetic stirrer. Nitrogen gas was passed through the drying tube and into the apparatus for 30 minutes, while heating the glassware with a heat gun to drive off residual moisture.

About 100 ml of anhydrous ethyl ether (Aldrich) was introduced to the addition funnel by cannula addition through a rubber septum. The ether was allowed to flow into the flask, and then 7.1 g of the benzophenone ether from Step C was added to the flask after removing the condenser and increasing the nitrogen flow. Methyl magnesium bromide, 10 ml (0.028 mole) of a 2.8 molar solution in ethyl ether (Aldrich), was charged to the addition funnel by a syringe through the septum, and allowed to flow drop-wise into the benzophenone ether solution in the flask. A white precipitate formed. The reaction mixture was allowed to stir 14 hours at ambient temperature.

The reaction mixture was poured into 100 ml of 25% aqueous ammonium chloride and stirred. An additional 50 ml of ethyl ether was added. The ether layer was collected using a separatory funnel, then dried over magnesium sulfate, and filtered. The ethyl ether was removed by rotary evaporation under reduced pressure to yield 7.4 g of orange liquid product containing 4-[3-[2-[2-(2-methoxyethoxy)ethoxy]ethoxy)ethoxy]ethoxy]propyl]-α-methylbenzhydrol. Purification steps were postponed until after dehydration. The analytical data, given below, were consistent with the assigned structure.

Infrared maxima of neat material: 3440, 3050, 2870, 1660, 1608, 1500, 1440, 1357, 1279, 1250, 1108, 940, 857, 761,700, and 607 cm$^{-1}$.

Figure 5:
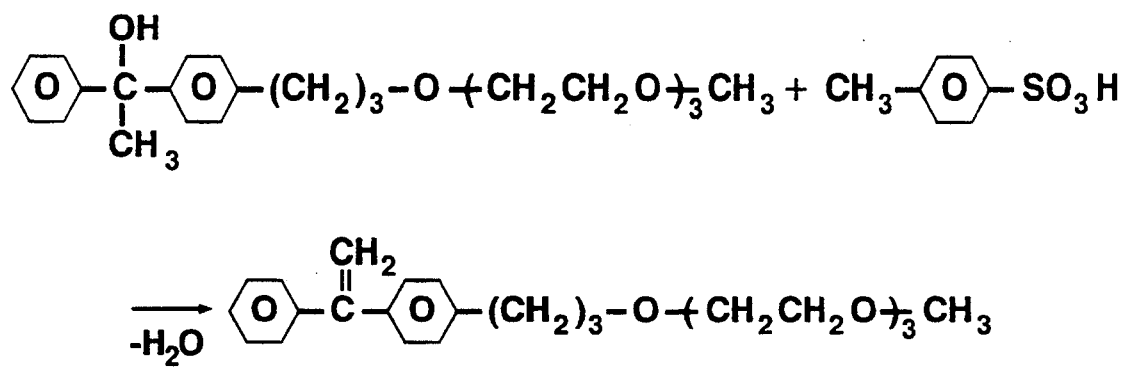

E. Dehydration of Tertiary Alcohol (FIG. 5)

A 250-ml, round-bottomed flask containing a magnetic stirring bar was equipped with a Dean-Stark trap and a Liebig condenser. A heating mantle was placed between the round-bottomed flask and a magnetic stirrer. About 150 ml of toluene was added to the flask, along with 7.4 g of the product from Step D. A spatula-tip amount of p-toluenesulfonic acid monohydrate (Aldrich) was added to the flask. The apparatus was wrapped in foil and heated to reflux temperature. After four hours of refluxing, about 0.5 ml of water was collected. The flask was placed in a refrigerator for 48 hours.

The toluene was removed by rotary evaporation under reduced pressure. A column separation was performed with 100–200 mesh silica gel and an eluant of 50/50 (v/v) hexane/ethyl acetate. The fractions which eluted were combined, and solvent removed by rotary evaporation, yielding 4.2 g of a light orange liquid.

A Kugelrohr distillation was performed on the residue to yield 4.0 g of 14[p-(1-phenylvinyl)phenyl]- 2,5,8,11-tetraoxatetradecane, a pale yellow liquid, b.p. 245° (0.05 mm Hg). The analytical data, given below, were consistent with the assigned structure.

Infrared maxima of neat material: 3548, 3050, 2860, 1664, 1610, 1500, 1436, 1350, 1300, 1232, 1179, 1115, 1025, 893, 843,781,703 cm$^{-1}$.

NMR (CDCl$_3$, 250MHz): 1.92 (m, 2H), 2.70 (t, 2H, J=7.4) 3.37 (s, H), 3.49 (t, 2H, J=6.5), 3.5–3.7 (m, 12H), 5.42 (d, 2H, J=0.1) and 7.13 –7.35 (m, 9H).

Elemental Analysis: Calculated for C$_{24}$H$_{32}$O$_4$ - C, 74.97; H, 8.39. Found - C, 74.02; H, 8.37.

EXAMPLE 2

Synthesis of α-Hydro-ω-[3-[p-(1-Phenylvinyl)phenyl]propoxy]-poly(oxyethylene)

A. Synthesis of 4-(3-Bromopropyl)benzophenone (FIG. 1)

The 4-(3-Bromopropyl)benzophenone was prepared as described in Step A, Example 1.

Figure 6:
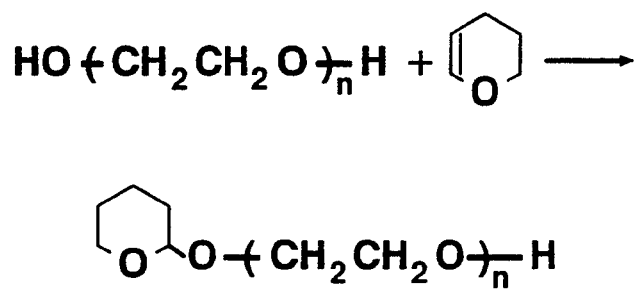

B. Protection of Polyethylene Glycol with 3,4-Dihydro-2H-pyran (FIG. 6)

A three-necked, 1000-ml, round-bottomed flask was equipped with a 125-ml pressure-equalizing addition funnel, a Liebig condenser, and a gas inlet valve. A football-type, teflon-coated stirring bar was placed in the flask. The addition funnel was capped with a rubber septum. A calcium sulfate (Drierite) drying tube was fixed to the top of the condenser, and Tygon ® tubing was used to connect the drying tube to a paraffin oil bubbler as described in Step A (Example 1). A heating mantle was placed between the round-bottomed flask and a magnetic stirring plate.

Dry nitrogen was passed through the Drierite ® column and into the system while the glassware was dried with a heat gun for thirty minutes.

The addition funnel was filled and emptied three times with anhydrous tetrahydrofuran (THF), using cannula transfer from an Aldrich ® Sure/Seal TM bottle. The nitrogen flow then was increased and the condenser removed to allow addition of 280 g (0.47 mole) of poly(ethylene glycol) 600 (Aldrich) and 15 g of pyridinium p-toluenesulfonate (PTS). Heat was applied to dissolve the PTS, and then 39 g (0.47 mole) of 3,4-dihydro-2H-pyran (DHP, Aldrich) was poured into the addition funnel. The drop-wise addition of DHP to the flask required several hours.

The pyridinium p-toluenesulfonate was prepared by swirling 17.1 g (90 mmoles) of p-toluenesulfonic acid monohydrate with 36 ml (450 mmoles) of pyridine at ambient temperature in a 100-ml round-bottomed flask for 20 minutes. Excess pyridine was removed in a rotary evaporator. White crystals formed which were dried in a vacuum oven overnight at 80°. The yield was 21 g (84%), m.p. 120°.

The reaction mixture was heated at reflux for 2.5 hours, then cooled. THF was removed by rotary evaporation, and cold ethyl ether was added to the reaction mixture to precipitate the PTS. After 2 hours of refrigeration, the reaction mixture was allowed to stand at ambient temperature to ensure liquification of the PEG component. The PTS then was removed by filtration through a medium fritted-glass funnel and washed once with ether; the wash was combined with the tiltrate. Ether was removed from the tiltrate by rotary evaporation under reduced pressure, yielding 287 g of α-hydro-ω-[(tetrahydro2H-pyran-2-yl)oxy]poly(oxyethylene)

(90%). The analytical data, given below, were consistent with the assigned structure.

Infrared maxima of neat material: 3375, 2875, 1630, 1454, 1348, 1303, 1258, 1120, 960, 862, 692, and 585 cm$^{-1}$.

Figure 7:
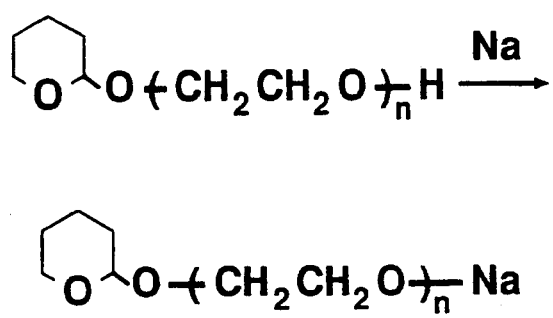

C. Alkoxylation of Protected Poly(ethylene glycol) (FIG. 7)

A 1000-ml, three-necked, round-bottomed flask was equipped as in Step A (Example 1). The product from Step B of this example, 227 g (0.405 mole), was added to the flask, along with 350 ml of anhydrous THF. Pieces of metallic sodium (Alfa Products Co., Ward Hill, Mass.) were cut and weighed, protected from atmospheric moisture by a thin coating of oil from the original container. The oil-coated sodium (10.2 g) was placed in hexane (9.3 g sodium, 0.405 mole). Nitrogen flow was increased, and the sodium was added in piecewise to the flask through the center neck. Heat was applied and reflux established to increase reaction of the sodium with the protected poly(ethylene glycol). Hydrogen evolved, and the reaction mixture gradually turned dark brown. After an 8-hour reflux period, about 1 g of sodium remained unreacted. This sodium was removed with forceps while in a dry box and destroyed by slow reaction in 2-propanol at ambient temperature. The reaction mixture, containing $\alpha$-sodio-$\omega$-[(tetrahydro-2H-pyran-2-yl)oxy]poly(oxyethylene), was used directly for the next step without purification. The analytical data, given below, were consistent with the assigned structure.

Infrared maxima of neat material: 2900, 1630, 1454, 1348, 1303, 1258, 1120, 960, 862, and 585 cm$^{-1}$.

Figure 8:
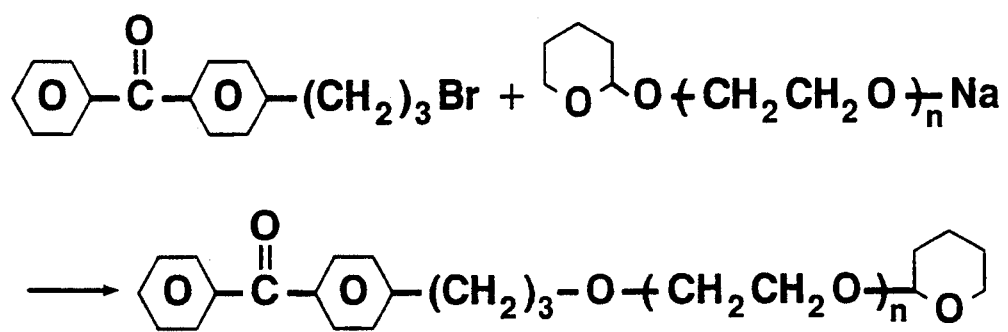

D. Williamson Ether Synthesis (FIG. 8)

The round-bottomed flask containing the alkoxide from Step C was refitted with a condenser, nitrogen inlet, and a 125-ml addition funnel. The 4-(3-bromopropyl)benzophenone, 103 g (0.34 mole) from Step A was added drop-wise by means of the addition funnel, and the mixture was heated at reflux temperature for eight hours, during which the color changed from dark brown through orange to an opaque yellow. The reaction mixture was allowed to stir at ambient temperature for 48 hours.

The reaction mixture then was centrifuged in portions, yielding an orange, clear supernatant. The precipitated sodium bromide was washed twice with THF and discarded. The supernatants were then combined and THF removed by rotary evaporation.

To remove any unreacted 4-(3-bromopropyl)benzophenone from the residue, the crude product was subjected to a silica column separation using 90% hexane/10% ethyl acetate (by volume) as eluant. After solvent removal, about 50 g of 4-(3-bromopropyl)benzophenone was recovered. The column then was washed with methanol to remove the desired product, and the methanol was removed by rotary evaporation. To remove any unreacted polyethylene glycol from the product, a toluene/water extraction was performed. The desired benzophenone ether, $\alpha$-[3-(p-benzoylphenyl)propyl]-$\omega$-[(tetrahydro-2H-pyran-2yl)oxy]-poly(oxyethylene), was concentrated in the toluene layer. After toluene removal, an orange liquid was obtained, approximately 120 g (88% yield, taking into account the recovered starting material). The analytical data, given below, were consistent with the assigned structure.

Infrared maxima of neat material: 3509, 2875, 1660, 1606, 1440, 1353, 1279, 1116, 940, 855, and 699 cm$^{-1}$.

NMR (CDCl$_3$, 250 MHz): 1.6 (m, 5H), 1.94 (m, 2H, J=7.4), 2.79 (t, 2H, J=7.5), 3.49 (t, 3H, J=6.5), 3.65 (m, 51H), 3.85 (m, 2H), 4.63 (m, 1H), and 7.3–7.8 (m, 9H).

Elemental Analysis: Calculated for C$_{44}$H$_{72}$O$_{16}$ - C, 61.68; H, 8.41. Found - C, 61.10 and 60.73; H, 8.61 and 8.79.

Figure 9:
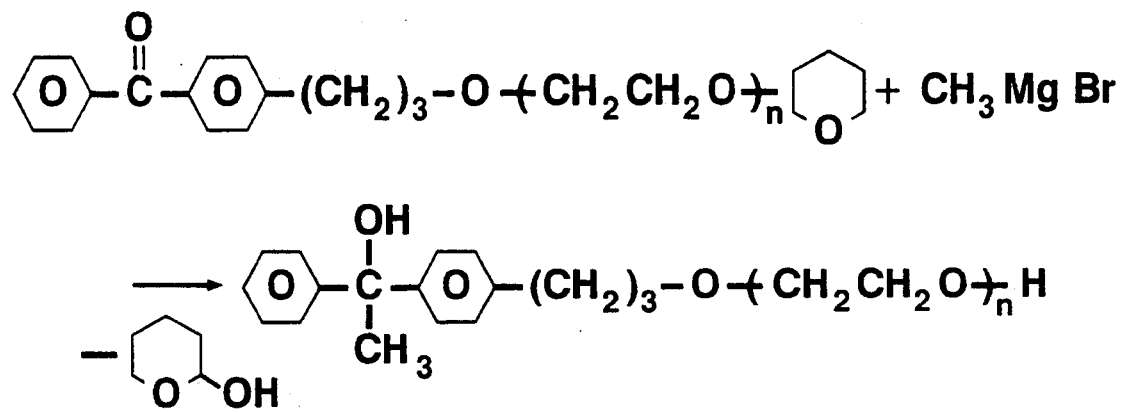

E. Synthesis of Tertiary Alcohol By Grignard Reaction (FIG. 9)

The Grignard reactions were carried out with small amounts (less than 30 g) of compound to avoid moisture contamination.

A 250-ml, three-necked, round-bottomed flask was equipped with a 125-ml, pressure-equalizing addition funnel, a nitrogen inlet, and a Liebig condenser with drying tube. A small magnetic stirring bar was placed in the flask. A cork ring was placed between the flask and the magnetic stirrer. The glassware was dried with a heat gun for 30 minutes with nitrogen flow. The ether product from Step D (27 g, 0.03 mole) was added to the flask, along with about 150 mL of anhydrous THF by cannula transfer. Then 15 ml (0.045 mole) of 3 molar methyl magnesium bromide in ethyl ether was added by syringe through a rubber septum into the addition funnel. The Grignard reagent was added drop-wise to the flask. Two hours after this addition, 2 ml of additional Grignard reagent was added; no additional reaction was apparent. The reaction mixture was allowed to stir 10 hours under nitrogen at ambient temperature.

THF was removed by rotary evaporation, leaving an orange, gummy residue in the flask. This residue was added to 600 ml of a 25% ammonium chloride (w/v) aqueous solution. After 1 hour of stirring, 200 ml of chloroform was added to the ammonium chloride solution. The chloroform layer sank to the bottom, carrying yellow organics with it. The chloroform layer was isolated by means of a separatory funnel and dried over anhydrous magnesium sulfate. After solvent removal, the yield was 24 g (96%) of tertiary alcohol, $\alpha$-hydro-$\omega$-[3-[p-($\alpha$-hydroxy-$\alpha$-methylbenzyl)phenyl]propoxy]-poly(oxyethylene). The analytical data, given below, were consistent with the assigned structure.

Infrared maxima of neat material: 3416, 3051, 2875, 1454, 1348, 1303, 1258, 1108, 948, 839, 754, and 699 cm$^{-1}$.

NMR(CDCl$_3$, 250MHz): 1.2–1.8ppm (m, 7H), 1.84 (m, 4H), 2.65 (t, 2H, J=7.6 Hz), 3.48 (t, 2H, J=6.8 Hz), 3.64 (m, 44H), 3.85 (m, 3H) 4.63 (m, 1H), 7.1–7.4 (m, 6H).

Elemental Analysis: Calculated for C$_{45}$H$_{76}$O$_{16}$ - C, 61.93; H, 8.72. Found - C, 61.26 and 61.38; H, 8.99 and 8.49.

Figure 10:
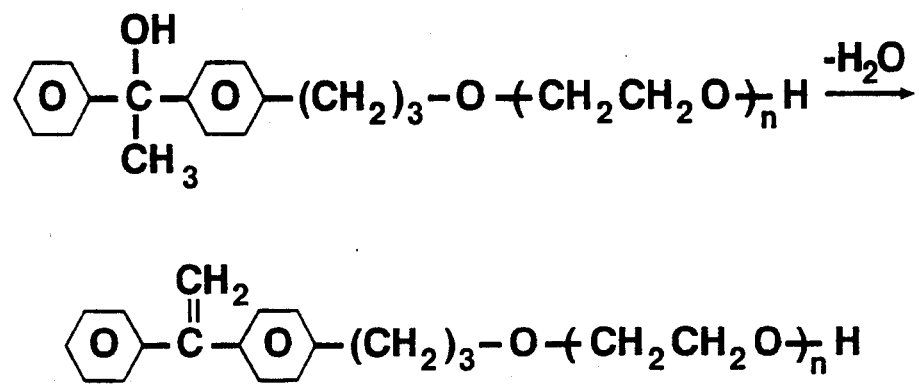

F. Dehydration of Tertiary Alcohol (FIG. 10)

A 500-ml, round-bottomed flask was equipped with a Dean-Stark trap and Liebig condenser; a magnetic stirring bar was placed in the flask. A heating mantle was placed between the flask and a magnetic stirrer. About 350 ml of toluene was added to the flask, along with 24.0 g of the Grignard product from Step E. A spatula-tip amount (approximately 10 mg) of p-toluenesulfonic acid monohydrate was added to the flask. The apparatus was wrapped in foil and heat applied. After four hours of heating at reflux temperature, about 0.6 ml of water had accumulated in the trap. There was no further accumulation of water after an additional hour.

The toluene was removed by rotary evaporation. To remove the p-toluenesulfonic acid. the residue was subjected to a column separation using 100–200 mesh silica gel and an eluant consisting of 90% hexane and acetate, by volume. Methanol was used to rinse the column, and after methanol removal a toluene/water extraction was performed as in Step D. Removal of the toluene left an orange liquid. This orange liquid was dissolved in chloroform and swirled with decolorizing carbon before elution through a 100–200 mesh silica column. The yield was 20 g (85%) of α-hydro-ω-[3-[p-(1-phenylvinyl)phenyl]propoxy]poly(oxyethylene). The analytical data, given below, were consistent with the assigned structure.

Infrared maxima of neat material: 3432, 3051, 2875, 1653, 1606, 1454, 1348, 1303, 1258, 1108, 948, 839, 777, 699, and 585 cm$^{-1}$.

NMR(CDCl$_3$, 250 MHz): 1.91 (m,2H), 2.70 (t, 2H, J=7.6 Hz), 3.48 (t, 3H, J=6.5), 3.64 (m, 54 H), 5.41 (dd, 2H, J=9.6, 0.88), and 7.1–7.3 (m, 10H).

Elemental Analysis: Calculated for $C_{45}H_{74}O_{15}$ - C, 63.23; H, 8.67. Found - C, 64.85 and 64.82; H, 8.12 and 8.29.

EXAMPLES 3 and 4

Electron Beam Grafting of the Compounds of Examples 1 and 2 to a Polypropylene Meltblown Web The fabric used for all electron beam grafting experiments was made from Exxon 3145 polypropylene in accordance with standard meltblowing techniques. See, for example, U.S. Pat. Nos. 3,704,198, 3,755,527, 4,663,220, and 4,820,577, which are incorporated herein by reference. No additives were used, and the fabric was unbonded. The meltblowing die utilized a 30 hole-/inch die tip in super recess condition. The basis weight was about 37 g/m$^2$.

Samples of the meltblown polypropylene fabric were cut with a paper cutter to about 23×10 cm, and then weighed on an analytical balance. Each sample was soaked five minutes in a 3% by weight solution of a compound of the present invention in methanol. The sample was removed from the solution with forceps and excess methanol was allowed to evaporate from the fabric for two minutes in a fume hood, after which each sample was wrapped flat in aluminum foil and packaged in plastic bags.

Each sample was treated with 10 Mrads of 175-keV electron beam radiation on both sides under a nitrogen atmosphere, using a Pilot 200 Electrocurtain ® System (Energy Sciences Inc., Woburn, Mass.) in accordance with the manufacturer's instructions.

Each sample then was dipped repeatedly in methanol to remove any unreacted compound, and air-dried. The dry weight was measured and compared to the initial dry weight to get percent add-on of surfactant, as follows:

$$\text{Percent add-on} = \frac{\text{final dry weight} - \text{initial dry weight}}{\text{final dry weight}} \times 100$$

In each case, the add-on of compound was 3 percent by weight.

Although the fabric to which the compound of Example 1 was grafted (Example 3) was wettable, drops of water placed on the fabric were absorbed after about 10 seconds. Fabric to which the compound of Example 2 was grafted (Example 4) was immediately wettable with water. That is, water drops placed on the top of the sample in different locations took on average less than 1 second to soak completely into the web.

EXAMPLES 5 AND 6

Preparation of Control Webs

Two control webs were prepared which utilized the same fabric and sample size as in Example 3. The first control web (Example 5) involved the use of the grafting procedure of Example 3, but with 2-hydroxyethyl methacrylate in place of a compound of the present invention. Samples of the meltblown polypropylene fabric were weighed and then soaked in a 75% (w/w) 2-hydroxy-ethyl methacrylate (Aldrich) in methanol solution. After five minutes of soaking, the samples were removed and exposed to electron beam radiation as described in Example 3. Add-on of 2-hydroxyethyl methacrylate was 19 percent by weight (Example 5A). The procedure was repeated with a more dilute solution to give a fabric having 3 percent by weight add-on (Example 5B).

The second control web (Example 6) involved simply treating fabric with Triton ®X-102. Weighed samples were prepared by soaking the meltblown fabric samples in a 0.5% (w/w) Triton ® X-102 (Rohm & Haas, Philadelphia, Pa.) in methanol solution for 30 seconds. The samples were removed with forceps, air-dried, and weighed. The level of surfactant add-on was 3 percent by weight.

Each of the control webs was tested for wettability as described for Examples 3 and 4. In each case, the web was immediately wettable.

EXAMPLE 7

Vertical Wicking Study

Fabric samples from Examples 4, 5, and 6 were chosen for a comparison study of vertical wicking rates. For the test, a 23×10 cm fabric sample was weighed, then taped to one half of a plastic-framed, screened fabric holder, such that the bottom of the fabric sample was even with the bottom of the sample holder. The covering half of the holder then was clamped to the bottom half, thereby enclosing the fabric sample in a sandwich-like fashion, while allowing air movement through the screens. The holder was suspended by the upper grip of a Model 1122 Instron Universal Testing Instrument (Instron Corporation, Canton, Mass.) and then lowered until contact was made between fabric and a synthetic urine, having a surface tension of about 55 dynes/cm, which was dyed with a small amount of red food coloring. A stopwatch was used to measure time (minutes), while average distance (cm) travelled by the fluid front was read from a transparent ruler attached to the holder. At the end of fifteen minutes the holder was quickly raised and dismantled so that the sample could be weighed to get the weight of synthetic urine pick-up. Capacity, expressed as a percentage, was then calculated by the equation:

$$\text{Capacity} = \frac{\text{wet weight} - \text{dry weight}}{\text{dry weight}} \times 100$$

The fabric samples were allowed to air-dry at ambient temperature over a 24-hour period. The wicking procedure then was repeated to evaluate the rewet effectiveness of each fabric. The results are summarized in Table 1; in the table, "VWD" represents vertical wicking distance.

TABLE 1

| | | \multicolumn{5}{c}{Treated Fabric Vertical Wicking Study Results} |
|---|---|---|---|---|---|

| Example Fabric | Add-on (%) | VWD (cm) 1st Wet | VWD (cm) Rewet | Capacity (%) 1st Wet | Capacity (%) Rewet |
|---|---|---|---|---|---|
| 4 | 3 | 11 | 12 | 54 | 56 |
| 5A | 19 | 12 | — | 55 | — |
| 5B | 3 | 0.2 | 0.2 | 1 | 1 |
| 6 | 3 | 15 | 4 | 61 | 17 |

While the Triton ®-treated web clearly gave the best results in terms of both vertical wicking distance and capacity, it is equally clear that the surfactant is fugitive, giving poor results upon rewet. At the 3 percent add-on level, 2-hydroxyethyl methacrylate is almost nonfunctioning. The material works well at an add-on level of 19 percent, but clearly is not capable of remaining on the web. That is, the polymerized material is removed completely from the fabric by the first rewet. The compound of Example 2, on the other hand, provided good vertical wicking and capacity, both with the first wetting and on rewet.

Having thus described the invention, numerous changes and modifications thereof will be readily apparent to those having ordinary skill in the art without departing from the spirit and scope of the present invention.

What is claimed is:

1. A compound of the formula:

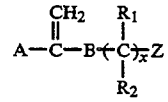

in which:
(a) each of A and B independently is phenyl which may be unsubstituted or substituted;
(b) each of $R_1$ and $R_2$ independently is hydrogen or $C_1$–$C_6$ alkyl;
(c) x represents an integer of from 0 to about 18; and
(d) Z is poly(alkyleneoxy) which may be uncapped or capped with a $C_1$–$C_6$ alkyl group;

which compound is adapted to be grafted by electron beam radiation to fibers and nonwoven webs in order to render them hydrophilic.

2. The compound of claim 1, in which both A and B are unsubstituted.

3. The compound of claim 1, in which Z is represented by the general formula,

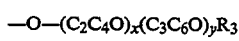

in which x represents an integer of from about 3 to about 18, y represents an integer of from 0 to about 9, the ratio of x to y is equal to or greater than 2; the sum of x and y is equal to or less than about 18; and $R_3$ is hydrogen or $C_1$–$C_6$ alkyl.

4. The compound of claim 3, in which $R_3$ is methyl, y is zero, and x represents an integer in the range of from about 7 to about 14.

* * * * *